United States Patent [19]

Neufeld

[11] Patent Number: 4,569,589
[45] Date of Patent: Feb. 11, 1986

[54] LUNG WATER COMPUTER SYSTEM

[75] Inventor: Gordon R. Neufeld, Philadelphia, Pa.

[73] Assignee: University of Pennsylvania, Philadelphia, Pa.

[21] Appl. No.: 497,941

[22] Filed: May 25, 1983

[51] Int. Cl.[4] .......................... G01N 33/48; G01J 3/50
[52] U.S. Cl. ........................................ 356/39; 356/72; 356/418
[58] Field of Search .................... 356/72, 410, 418, 39, 356/40, 41, 42

[56] References Cited

U.S. PATENT DOCUMENTS

| 3,614,452 | 10/1971 | Felton | 356/410 |
|---|---|---|---|
| 3,787,124 | 1/1974 | Lowy et al. | 356/414 |
| 3,794,425 | 2/1974 | Smith et al. | 356/418 X |
| 3,807,873 | 4/1974 | Nakamori | 356/418 |
| 3,844,661 | 10/1974 | Birkett et al. | 356/418 X |
| 3,851,175 | 11/1974 | Dahlin et al. | 250/343 |
| 3,860,344 | 1/1975 | Garfunkel | 356/418 X |
| 3,972,614 | 8/1976 | Johansen et al. | 356/73 |
| 4,006,358 | 2/1977 | Howarth | 250/341 |
| 4,083,367 | 4/1978 | Porter et al. | 128/2.07 |
| 4,090,792 | 5/1978 | Bunge | 356/418 |
| 4,093,385 | 6/1978 | Noboru | 356/418 |
| 4,134,678 | 1/1979 | Brown et al. | 356/40 |
| 4,233,513 | 11/1980 | Elder et al. | 250/343 |
| 4,236,075 | 11/1980 | Nexo et al. | 250/351 |
| 4,443,108 | 4/1984 | Webster | 356/418 |
| 4,466,544 | 8/1984 | Satake et al. | 356/418 X |

OTHER PUBLICATIONS

Skylab S191 Visible-Infrared Spectrometer, T. L. Barnett and R. D. Juday, Applied Optics, pp. 967–972, Apr. 1977.
Synchronous Detection of Deuterium Oxide and Indocyanine Green in Flowing Blood, Journal of Applied Physiology, pp. 1367–1371, G. Basset, G. Martet, F. Bouchonnet, J. Marsac, J. Sutton, F. Botter, and R. Capitini, 1981.

Primary Examiner—Vincent P. McGraw
Assistant Examiner—S. A. Turner
Attorney, Agent, or Firm—Seidel, Gonda, Goldhammer & Abbott

[57] ABSTRACT

A lung water computer system utilizing a single optical detection path. A single beam of visible (VIS) and infrared (IR) radiation is chopped and filtered in at least two bandwidths centered on the absorption peaks of tracers such as indocyanine green (ICG) and deuterated water (DHO). The chopped, filtered beam is transmitted along the optical detection path to a densitometer cell provided with intersecting fluid and optical channels. The optical channels are milled to provide an accurate optical path length (OPL) across the fluid channel. The chopped filtered radiation traverses blood containing ICG and DHO in the fluid channel and is detected by a two color (VIS and IR) detector at the end of the optical detection path. The VIS and IR outputs of the detector are processed in separate electronic channels. The channels are sampled and the sample data is used to compute optical density, tracer concentration, cardiac output, tracer transit time, recovery factor and lung water according to well-known algorithms. Although not necessary in computing lung water, the channels may be sampled adaptively based on the sample levels or signal to noise ratio (S/N).

16 Claims, 19 Drawing Figures

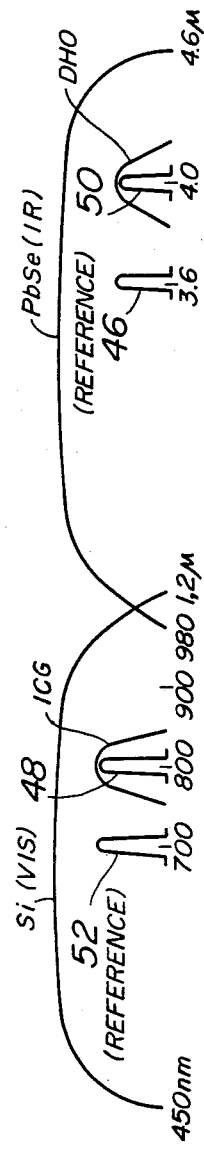
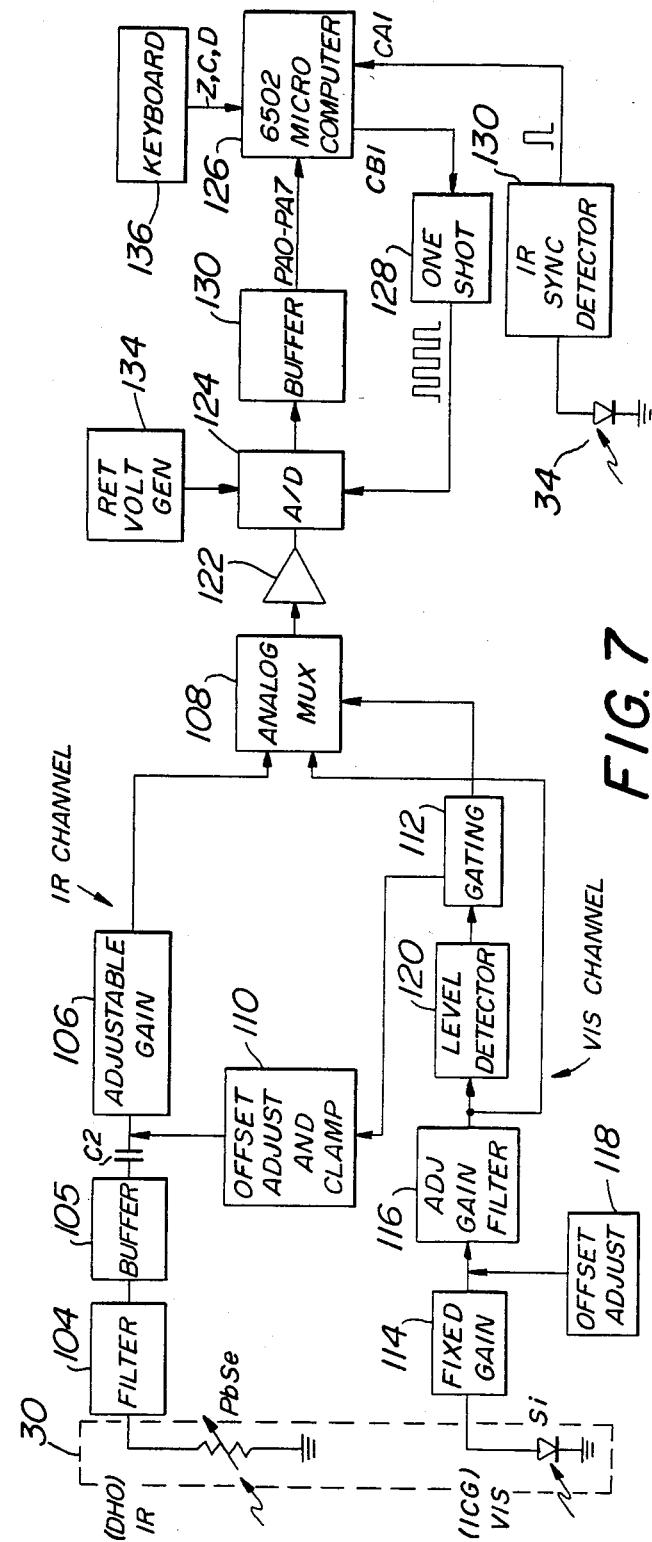
FIG. 6
FIG. 7

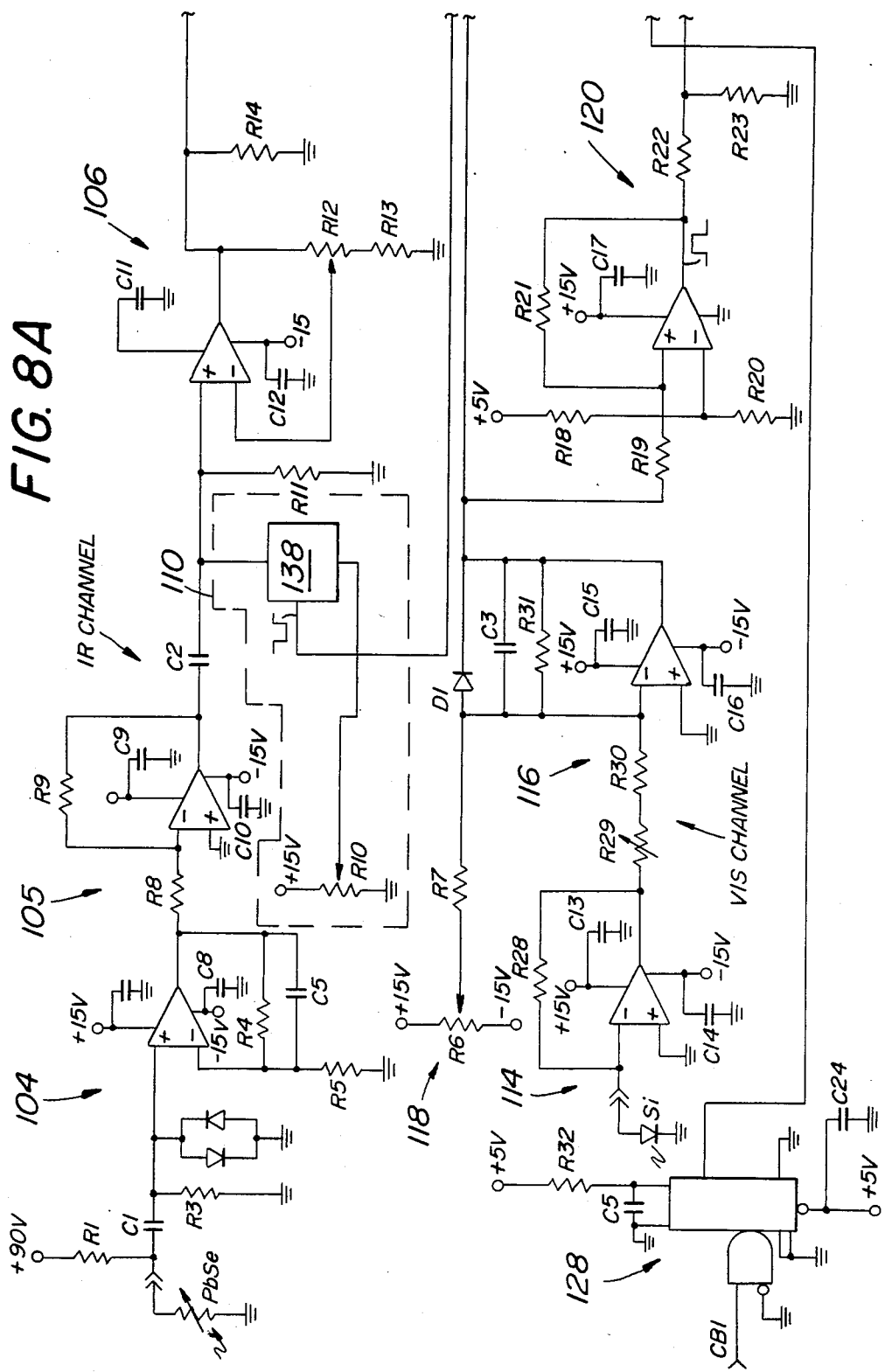

1

LUNG WATER COMPUTER SYSTEM

BACKGROUND OF THE INVENTION

The present invention is directed to a lung water computer system. In particular, the invention is directed to a software controlled data acquisition scheme for rapidly detecting concentrations of ICG and DHO tracers in a patient's blood over a relatively short interval of time such as 30 seconds. The invention may also be employed to detect constituents of food stuffs, gases, etc. The number of data samples may be varied adaptively over a wide range of sample levels or signal to noise (S/N) ratios.

The invention utilizes a single optical detection path and a single beam of VIS and IR radiation. The concentrations of DHO and ICG in the patient's blood are monitored over time and stored in memory to enable a software calculation of lung water.

Other systems for computing lung water using ICG and DHO tracers are known. Such systems, however, do not permit software control of data acquisition or adaptive control of the number of data samples. Such a system is disclosed in Basset et al, "Simultaneous Detection Of Deuterium Oxide And Indocyanine Green In Flowing Blood", Journal of Applied Physiology, pp. 1367–1371 (1981). In the Basset et al system, two separate beams are employed, one sample beam and one reference beam. The beams are identical. One beam is passed through a silica sample cell, and the other beam is passed through a reference cell which is an absorber of variable optical density. A mechano-optical device splits the beam passed by the cells into four beams, two sample beams and two reference beams. One sample beam and one reference beam are fed to a filter centered at an absorption peak of one tracer, and the other sample and reference beam are fed to an interference filter centered at the absorption wave length of the other tracer. The output of each filter is fed to an associated detector. One detector is a ICG detector, and the other detector is a DHO detector. The DHO detector may be a pyroelectric detector, and the ICG detector may be a silicon (Si) photodiode. The detector outputs are amplified by synchronous amplifiers and the amplified signals are plotted using a potentiometric recorder. The sampled recorded data is fed to a Commodore PET 2001 microcomputer to calculate flow rate, mean transit time, and lung water. The computer does not control the mode of data acquisition.

The system described in Basset et al suffers from certain disadvantages. Since two separate beams are employed, the system requires associated mechano-optics to split the beams into two separate optical channels. In addition, two separate detectors are required. Moreover, the silica sample cell is known to have a cut-off objectionably close to the DHO absorption peak (approximately 4.0 microns). Further, data acquisition is not computer controlled nor is it adaptive, that is, the number of samples is not variable as a function of sample level or S/N. In addition, the pyroelectric detector chosen for the Bassett et al system is slow responding (1–4 hz) in comparison to PbSe which can respond to a chopping rate up to 200 Khz.

The present invention also has application in the detection of other tracers or constituents of a fluid sample, in the detection of constituents of gases such as anesthetic gases, in the detection of minerals in an airborne ground scanning system, and in the detection of color and content of foodstuffs.

BRIEF SUMMARY OF THE INVENTION

A single beam of VIS and IR radiation is chopped and filtered at bandwidths centered on the absorption peaks of ICG and DHO tracers injected in a patient's blood. The blood is passed through a densitometer cell having intersecting fluid and optical channels defining an extremely accurate optical path length (OPL). The chopped, filtered radiation is transmitted through the fluid and optical channels and is detected by a two color VIS and IR detector at the end of a single optical detection path. The detector outputs are processed in separate electronic channels which are sampled under software control. The channels may be sampled by an adaptive technique wherein the number of samples accumulated depends on the sample level or S/N. The samples are summed and averaged. The averages are stored in a tracer memory array and are available to compute tracer concentration, cardiac output, tracer transit time, recovery factor and lung water.

An object of the invention is to provide a simple optical system which avoids multiple beam sources of VIS and IR radiation and multiple optical detection channels.

Another object of the invention is to provide a densitometer cell having an extremely accurate OPL.

Another object of the invention is to provide a flexible, software controlled data acquisition scheme for detecting the changing concentrations of constituents such as tracers in a fluid sample over relatively short periods of time such as 30 seconds.

Another object of the invention is to provide an adaptive data acquisition system for detecting changing concentrations of constituents such as tracers over wide fluctuations in sample level or S/N.

Another object of the invention is to provide an optical detection system wherein large numbers of tracers may be detected in a fluid sample utilizing a single optical detection path.

For the purpose of illustrating the invention, there is shown in the drawings a form which is presently preferred; it being understood, however, that this invention is not limited to the precise arrangements and instrumentalities shown.

BRIEF DESCRIPTION OF THE DRAWINGS

FIG. 6 is a diagram showing the spectral (wavelength) characteristics of the two color detector, the optical filters, and the ICG and DHO tracers.

FIG. 7 is a block diagram of the electronics showing the separate VIS and IR channels.

DETAILED DESCRIPTION OF THE INVENTION

Figure 1:
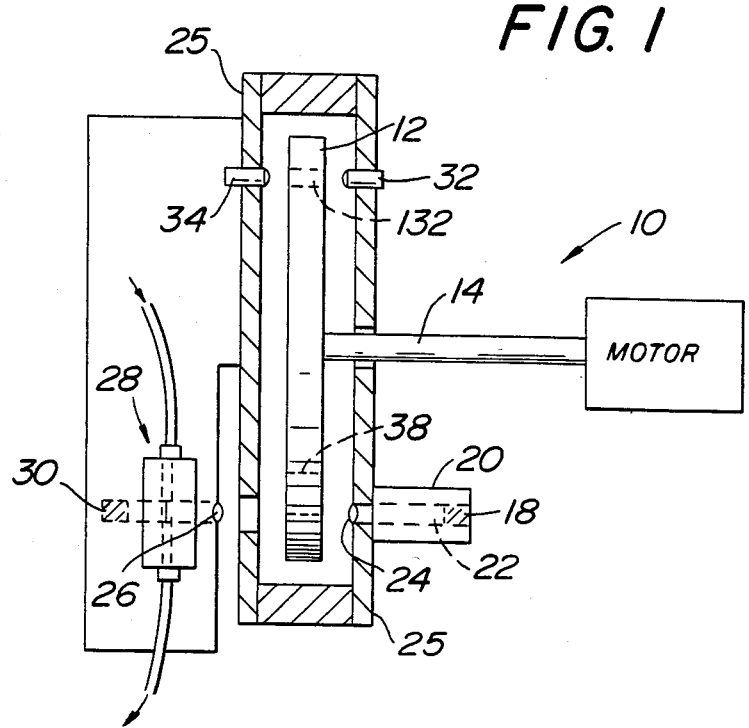
FIG. 1 is a diagrammatic representation of the mechano-optical portion of the invention showing the single optical detection path.

Referring to the drawings, wherein like numerals indicate like elements, there is shown in FIG. 1 the mechano-optical portion of the invention, designated generally as 10. Portion 10 includes a chopper/filter wheel 12 mounted on a shaft 14 driven by a synchronous motor 16 such as a model 709 Bodine Instrument motor. In the preferred embodiment, the motor is operated at 1800 rpm, although other operating speeds may be employed as will become evident from the ensuing description. A source 18 of VIS and IR radiation is mounted in a housing 20 provided with a bore 22. Source 18 may be a VIS and IR radiation source supplied by Astro, Inc. The VIS and IR radiation is collimated by a CaF2 lens 24 manufactured by Janos Optical, Inc. The housing 20 and lens 24 are mounted on a frame 25. The collimated VIS and IR beam is chopped and filtered, as described hereinafter, by chopper/filter wheel 12. The chopping rate is determined by the motor speed.

The chopped and filtered collimated beam is transmitted to a CaF2 collector lens 26 which collects the beam emanating from the wheel filters and transmits the beam to a densitometer cell 28. The densitometer cell is provided with intersecting fluid and optical channels which define an extremely accurate OPL as described hereinafter. Preferably, the OPL of the densitometer cell is 0.15 mm for the purpose of detecting ICG and DHO tracers in a blood sample flowing through the optical and fluid channels.

The chopped, filtered VIS and IR beam is transmitted through the cell 28 to a two color IR Industries, Inc., 9002 detector 30 containing in line, back to back optical sensors, namely, a PbSe photoresistor and a Si photodiode. An IR source 32 and IR detector 34 are mounted on frame 25 in facing relation on opposing sides of the chopper/filter wheel 12 for synchronizing the chopper/filter wheel and electronics as described hereinafter. Although not shown, the collector lens 26, densitometer cell 28 and two color detector 30 are mounted on suitable structure so as to align the collector lens, the densitometer cell OPL, and the two color detector with the chopped, filtered VIS and IR beam.

CHOPPER/FILTER WHEEL

Figure 2:
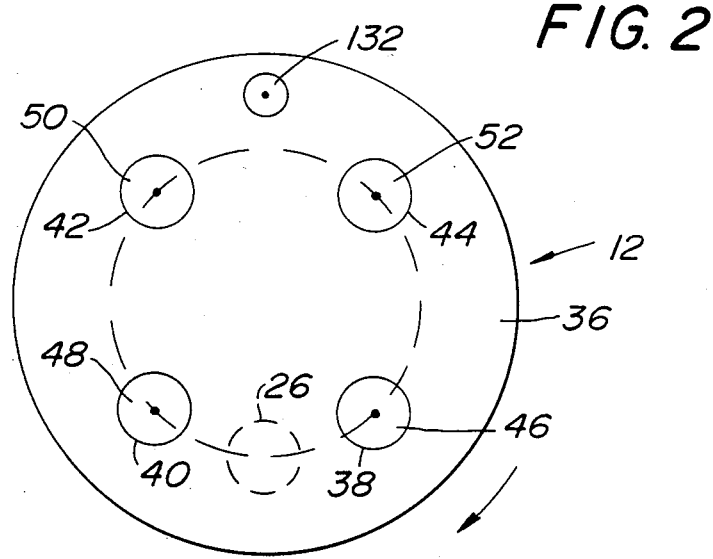
FIG. 2 is a diagrammatic representation of the chopper/filter wheel.

Referring to FIG. 2, the chopper/filter wheel 12 is shown in greater detail. In the preferred embodiment, the chopper/filter wheel 12 comprises a solid opaque disk 36 having four equi-spaced threaded holes 38, 40, 42 and 44 therein. Four IR Industries, Inc. optical interference filters 46, 48, 50 and 52 are mounted in threaded holes 38, 40, 42 and 44 respectively by means of threaded retaining rings (not shown). In general, the number of optical filters will correspond to the number of tracers which are to be detected in the fluid sample although in the preferred embodiment described herein four filters are employed to detect two tracers, ICG and DHO. Two filters are "sample" filters centered respectively on wavelengths corresponding to the ICG and DHO absorption peaks. The other two filters are "reference" filters which are centered respectively on wavelengths offset from the two absorption peaks. The reference filters are used to correct for drift in the VIS and IR source 18 and the VIS and IR electronic channels (described hereinafter) and to correct for changes in the optical density of the flowing blood in the VIS spectrum due to changes in red cell orientation under pressure fluctuation.

Referring to FIG. 6, VIS filters 48 and 52 have adjacent transmission bandwidths in the VIS spectrum, sample filter 48 being centered on the ICG absorption peak (approximately 800 nm) and reference filter 52 being centered on an adjacent bandwidth (approximately 700 nm). The other two filters, IR filters 46 and 50, have adjacent transmission bandwidths in the IR spectrum, filter 50 being centered on the DHO absorption peak (approximately 4.0 microns) and filter 46 being centered on an adjacent reference bandwidth (approximately 3.6 micrions). In the lung water computer system described herein, filter 46 may be eliminated without seriously affecting detection accuracy. It is preferred, however, that filter 52 be retained to correct for changes in optical density in the VIS spectrum.

DENSITOMETER CELL

Figure 3:
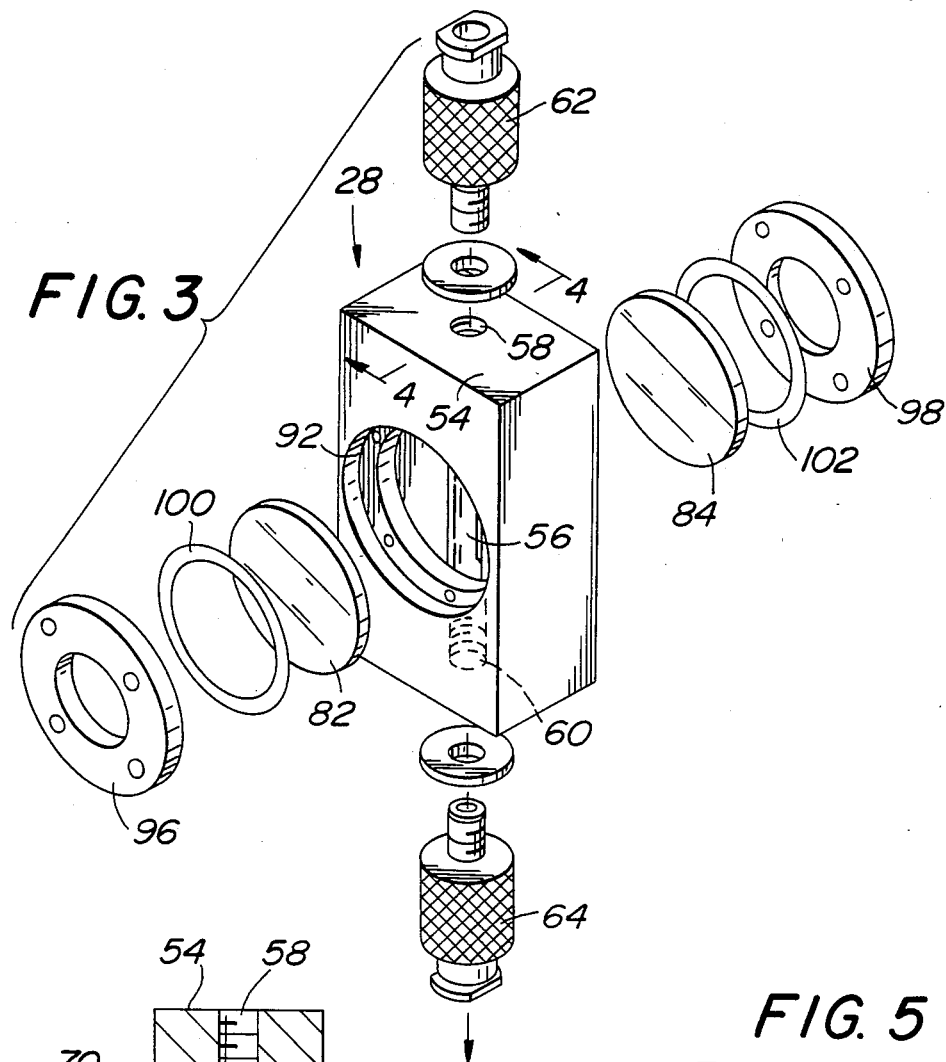
FIG. 3 is an exploded diagram of the densitometer cell.
Figure 4:
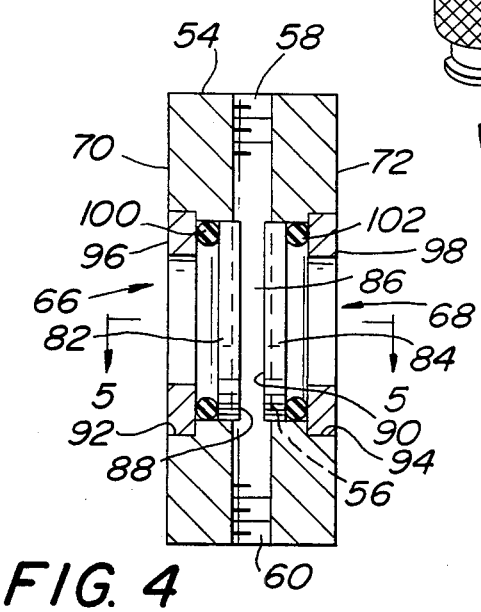
FIG. 4 is a cross-section taken along 4—4 in FIG. 3.
Figure 5:
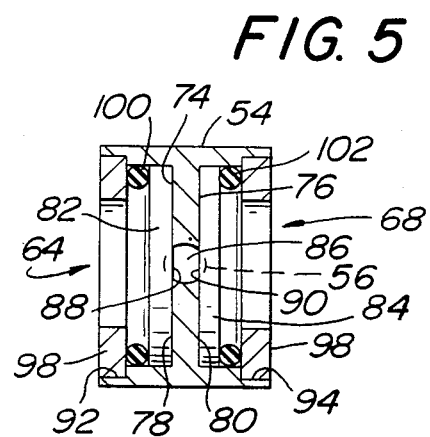
FIG. 5 is a cross-section taken along 5—5 in FIG. 4.

The densitometer cell is shown in detail in FIGS. 3–5. Referring to FIG. 3, the densitometer cell comprises a solid metal block 54. A cylindrical fluid channel 56 is bored through the block. Preferably, the channel 56 has a diameter of 3 millimeters. The upper and lower portions 58, 60 of the fluid channel are threaded so as to receive Luer connectors 62, 64 respectively. Blood is passed from a patient's artery through a 20 gauge catheter (not shown) coupled by a narrow gauge flexible conduit to Luer connector 62. The blood flows through the cell and is pumped by a roller tubing pump to a collector vessel (not shown) through narrow gauge conduit coupling the pump to Luer connector 64 on one side and the collector vessel on the other side. After a zeroing operation described hereinafter, the patient is injected with ICG and DHO in known concentrations. Concentrations of ICG and DHO in the blood are detected dynamically, that is, as a function of time. The entire detection process consumes very little time, in the order of 30 seconds, after which the densitometer cell is disconnected from the catheter. A calibrate operation is then performed. In the calibrate operation, a known quantity of the patient's blood (taken prior to injection) is recirculated through the densitometer cell via the roller tubing pump. The output port of the pump is connected by a narrow gauge conduit to the input port of the densitometer cell (Luer connector 62). A precise quantity of each tracer is added to the recirculating blood by injecting the tracer in an inlet injection port of the narrow gauge conduit.

The metal block 54 is provided with a pair of coaxial facing cylindrical optical channels 66, 68 milled on opposing sides of fluid channel 56 into the block side faces 70, 72 respectively. The optical channels 66, 68 have identical diameters, preferably 12 millimeters, and extend into the fluid channel 56 as shown in FIGS. 4 and 5. The optical channels define opposing planar shoulder surfaces 74, 76 and 78, 80. See FIG. 5. A pair of disk-shaped windows 82, 84, preferably sapphire, are placed flush against the shoulder surfaces within channels 66, 68. The fluid channel 56 and the facing surfaces 88, 90 of windows 82, 84 respectively define a zone 86 through which the blood flows. The chopped, filtered VIS and IR radiation passes through the blood flowing through the zone. The ICG tracer absorbs VIS radiation and the DHO tracer absorbs IR radiation in varying degrees depending on their concentrations.

The OPL of the zone is equal to the separation between the facing window surfaces 88, 90 which is in turn determined by the separation between surfaces 74 (78) and 76 (80). Thus, the OPL is determined by the depths of channels 66, 68. Preferably, the channel depths are identical and are chosen to obtain an OPL which is 0.15 millimeters. It should be appreciated, however, that a wide variety of OPLs can be obtained by milling the optical channels to different depths.

To seal the optical windows 82, 84 in position, threaded counterbores 92, 94 are milled into block 54 in coaxial alignment with channels 66, 68. A pair of retaining rings 96, 98 are screw-fastened to block 54 in counterbores 92, 94 respectively. The outer diameters (OD) of the retaining rings are substantially the same as the diameters of the counterbores. A pair of O-rings 100, 102 are sandwiched between the retaining rings and the associated optical windows. Zone 86, therefore, is tightly sealed, so that the assembled densitometer cell is leak-proof. The entire call may be easily disconnected from the fluid conduits and separately sterilized.

Preferably, in the ICG-DHO scheme described herein, the disk-shaped windows 82, 84 are sapphire windows such as Melles Griot windows which have a transmission bandwidth of approximately 300 nm (VIS)-6.0 microns (IR). Windows having other transmission bandwidths may also be employed, however, depending on the particular application and location (wavelength) of the tracer absorption peaks. For example CaF$_2$ windows may be substituted for the sapphire windows where it is desired to transmit longer wavelength IR through zone 86 corresponding to a tracer having an absorption peak for example in the far IR spectrum.

The construction of the densitometer cell 28 enables rapid disassembly so as to substitute windows having a wide variety of different transmission bandwidths. Thus, the densitometer cell may be easily assembled to obtain a particular OPL and transmission bandwidth by appropriate selection of the optical channel depths and the windows.

TWO COLOR DETECTOR

The two color detector 30 comprises VIS sensor which is a silicon (Si) photodiode and a IR sensor which is lead selenide (PbSe) photoresistor, both of which are mounted in a single TO5 transistor can. The Si photodiode and PbSe photoresistor are arranged in line, back to back, with the Si photodiode closest to cell 28. The Si photodiode is transparent to IR, transmitting the same to the PbSe photoresistor with virtually no radiation loss.

The spectral characteristics of the Si photodiode and PbSe photoresitor are shown in FIG. 6 in relation to the absorption peaks of the ICG and DHO tracers. The Si and PbSe curves represent the bandwidths over which the photodiodes and photoresistor are sensitive, i.e., the bandwidths at which they absorb radiation, and the absorption peaks of the ICG and DHO tracers represent the bandwidths at which the tracers absorb VIS or IR radiation resulting in an attendant loss of radiation at the detector.

BLOCK DIAGRAM

A block diagram of the electronic portion of the invention is shown in FIG. 7. The circuit includes separate IR and VIS channels. The IR channel processes IR samples and the VIS channel processes VIS samples.

IR CHANNEL

The PbSe photoresistor is connected to a low pass filter 104 in the IR channel. The filter has a suitable cut-off for rejecting noise. The output of the filter is connected to the input of a buffer 105 which drives an adjustable gain amplifier 106. The output of amplifier 106 is connected to one input channel of an analog multiplexor 108. The input of amplifier 106 is connected to an offset adjust and clamp circuit 110 which presets the dc offset of amplifier 106 in response to the output of a gating circuit 112 operated by the VIS channel as described hereinafter. The purpose of the dc offset is to ensure that the full output of a buffer amplifier 122 is within the range of an A/D converter 124.

VIS CHANNEL

The Si photodiode is connected to a fixed gain amplifier 114 in the VIS channel. The output of amplifier 114 is connected to an adjustable gain low pass filter 116 having a cut-off suitable for rejecting noise. The input of the filter is connected to an offset adjust circuit 118 which presets the dc offset of adjustable gain filter 116. The purpose of the dc offset is to ensure that the full output of buffer amplifier 122 is within the analog range of A/D converter 124. The output of the adjustable gain filter 116 is connected to a level detector 120 and to the other input channel of multiplexor 108.

When VIS radiation is transmitted to the Si photodiode by optical filter 48 or 52, as indicated by the output of the level detector, gating circuit 112 causes the analog multiplexor 108 to transmit the adjustable gain filter 116 output to the input of buffer amplifier 122 while disconnecting the IR channel from the buffer amplifier input. Thus, the IR channel is cut-off or pre-empted. At the same time, the gating circuit causes the offset adjust and clamp circuit 110 to preset the dc offset of adjustable gain circuit 106. The dc offset is held by capacitor C2.

If no VIS radiation is transmitted to the Si photodiode, as indicated by the output of the level detector, the gating circuit 112 causes the offset adjust and clamp circuit 110 to release the input of adjustable gain circuit 106, but the dc offset is held by capacitor C2. The gating circuit also operates analog multiplexor 108 at this time so as to transmit the output of adjustable gain circuit 106 to buffer amplifier 122. The output of the buffer amplifier is nominally zero, however, until IR radiation is transmitted to the PbSe photoresistor by optical filter 46 or 50.

From the foregoing, it should be appreciated that multiplexing between the IR and VIS channels is accomplished based on the presence or absence of VIS radiation at the Si photodiode as determined by the positions of the optical filters 48 or 52 relative to lens 26. Accordingly, the time control for the multiplexor is determined by the synchronized to the speed of the chopper/filter wheel.

The output of buffer amplifier 122 is a time multiplexed analog signal derived from the chopped and filtered VIS and IR. The amount of chopped and filtered VIS and IR radiation transmitted to the VIS and IR detectors is a function of the ICG and DHO concentrations. Representative concentrations are shown in phantom in FIGS. 11a and b. The output of the buffer amplifier comprises consecutive analog samples of the VIS and IR detector outputs. The buffer amplifier output is repetitively sampled and converted to digital at a relatively high frequency by an AD7574 A/D convertor 124 (FIG. 7). The sampling rate of the A/D convertor is controlled by the CB1 output of a 6502 microprocessor 126 via a 74LS221 one shot 128. The digital output of A/D convertor 124 is transmitted by a 74CZ44N buffer circuit 129 to the PA0-PA7 data inputs of the microprocessor.

Figure 11:
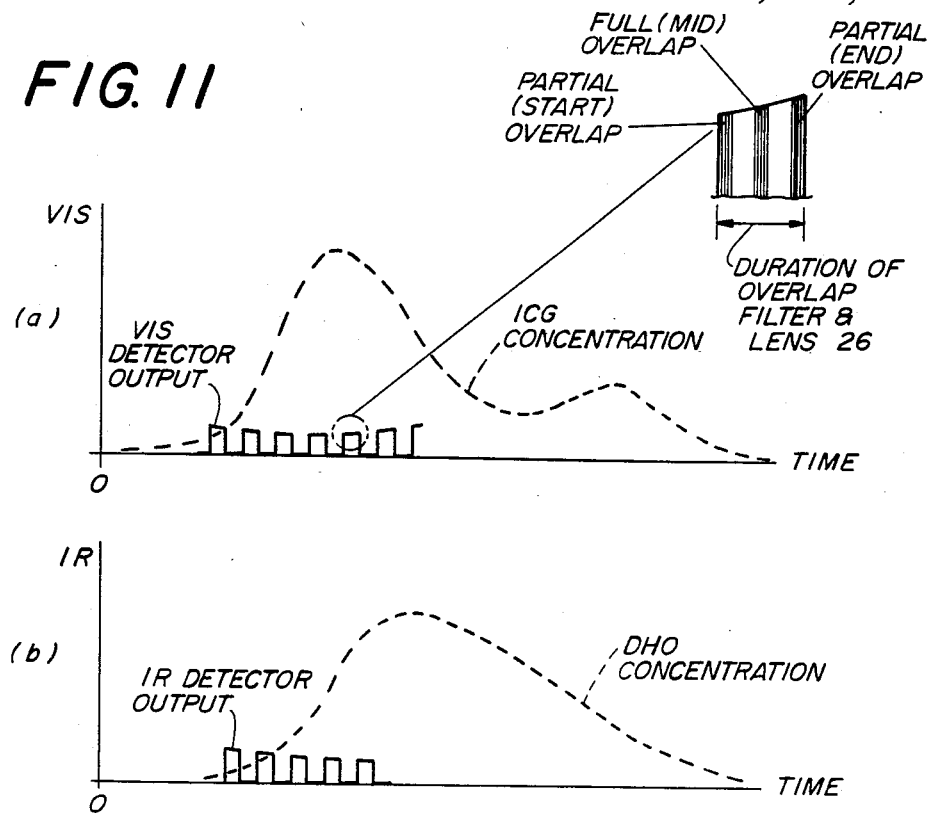
FIGS. 11a and b are diagrams of representative ICG and DHO concentrations and VIS and IR detector outputs as a function of time.

The A/D convertor operation is synchronized to the chopper/filter wheel 12 by means of IR source 32 and IR detector 34. The IR detector 34 is a TIL 78 photodiode which is connected to an IR sync detector circuit 130. The IR source and detector face each other on opposite sides of the chopper/filter wheel 12 (FIG. 1). A synchronizing opening 132 in the wheel traverses the source and detector at each revolution of the wheel. When opening 132 moves into alignment with the source and detector, the IR sync detector circuit 130 is triggered to produce a pulse at the CA1 input of the microprocessor. In response to the CA1 pulse, the microprocessor generates a high frequency pulse train at its CB1 output. As described more fully hereinafter, the pulse repetition frequency (PRF) of the CB1 pulse train may be 3 Khz, 30 Khz or other suitable value. The microprocessor continuously counts the CB1 pulses. Each filter moves into overlapping relation with lens 26 a predetermined interval of time following the CA1 pulse. The waiting period is determined by the speed of wheel 12 and the spacing between the optical filters. At the end of each waiting period, as indicated by the count of CB1 pulses, a filter reaches the desired overlapping relation with lens 26. Collection of the digital outputs of the A/D converter by the microprocessor is initiated at the end of each waiting period. As shown in FIG. 11a, collection of the A/D converter outputs may be initiated any time during overlap of the filter and lens 26 by appropriate choice of the waiting period. For example, sample collection may be initiated at or near the initial period of overlap, at or near the point of complete overlap, or at or near the terminal period of overlap. In addition, sample collection may occur over the entire period or any portion of the period of overlap by appropriate choice of the PRF of the CB1 pulses and the number of samples to be collected for each filter.

The CB1 pulses are squared up by one shot 128 and fed to the A/D converter. At each pulse, the A/D converter samples the multiplexed analog output of buffer amplifier 122 and converts the sample to a multiple bit digital signal. The analog conversion range of the A/D converter is set by a reference voltage generator 134 in conventional manner. The number of samples to be collected by the microprocessor following the predetermined waiting interval for each optical filter on wheel 12 is programmed into the microprocessor and may be a constant or a variable based on sample level or S/N as described hereinafter. Each digitized sample is transmitted to the microprocessor by buffer 129 for storage and processing.

In the lung water computer system described herein, the A/D converter is controlled by the microprocessor to acquire data in a ZERO, CALIBRATE or DATA ACQUISITION mode as described more fully hereinafter. The mode of operation is selected by the operator at a keyboard 136. The keyboard output lines "Z", "C" and "D" indicate the selected mode.

DETAILED ELECTRONICS

Figure 8B:
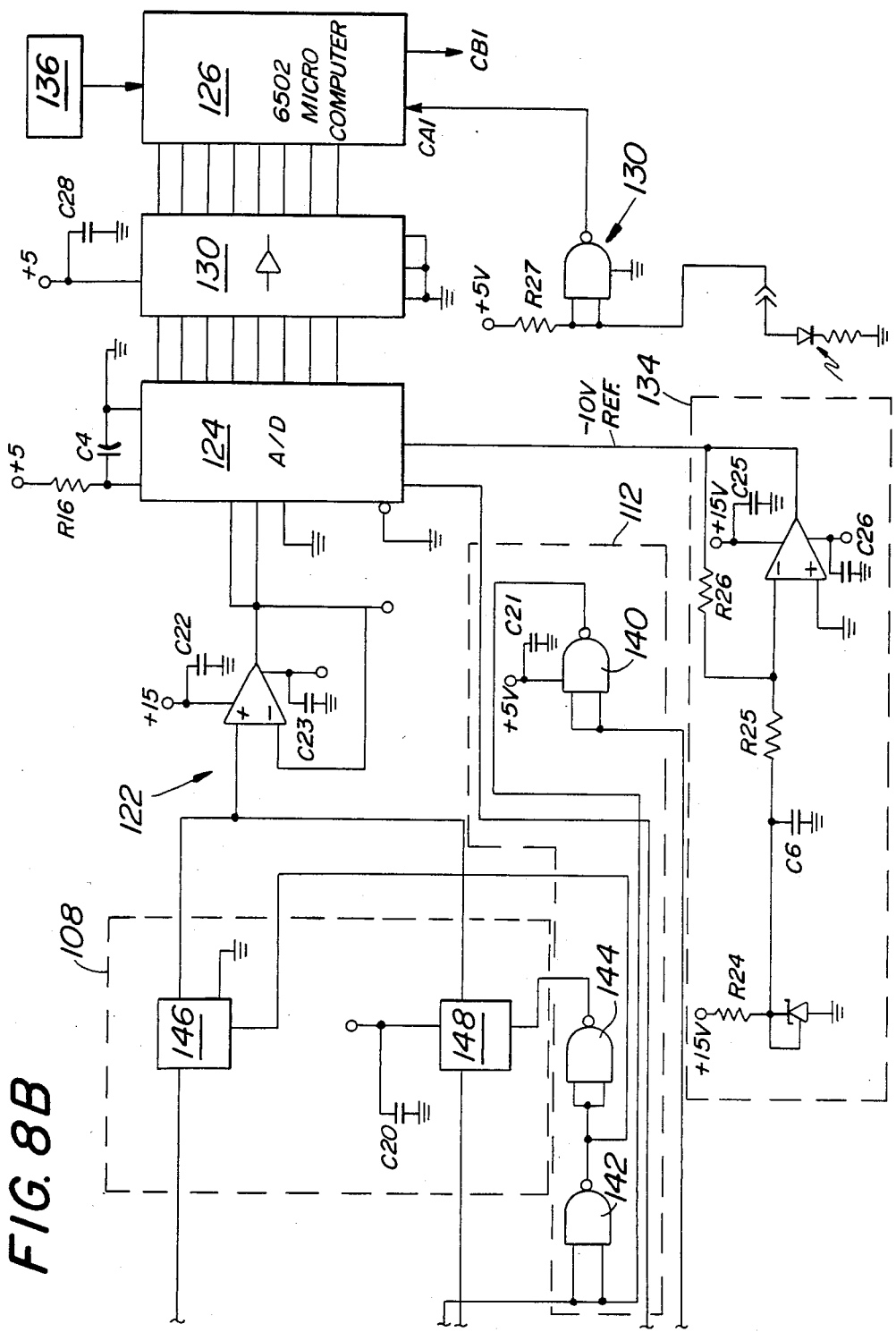
FIGS. 8a and b comprise a detailed schematic of the electronics.

Referring to FIGS. 8A and B, there is shown a detailed schematic of the electronics corresponding to the block diagram of FIG. 7. Each of the components disclosed in FIG. 7 is indicated by corresponding numerals in FIGS. 8A and B. The input section of the electronics is divided into IR and VIS channels which separately process the IR and VIS information.

IR CHANNEL

The IR channel includes the PbSe photoresistor connected via 300 k resistor R1 to a +90 v dc supply. The photoresistor voltage is ac coupled by a 1 microfarad capacitor C1 to the low pass filter 104. The filter comprises a LM356 operational amplifier. The gain-frequency curve of the low pass filter is determined by 100 K resistor R4, 0.01 microfarad capacitor C5, and 1 K resistor R5. The gain is approximately 100 from 0hz to the cut-off, tapering to unity gain near the cut-off. The output of filter 104 is transmitted to buffer circuit 105. The buffer circuit comprises a LM356 operational amplifier connected for unity gain inversion. Thus, 10 K resistors R8 and R9 are connected to the inverting input of the amplifier. The output of the buffer 105 is AC coupled to the noninverting input of adjustable gain amplifier 106. The adjustable gain amplifier comprises a LM356 operational amplifier. The inverting input of the operational amplifier is connected to the wiper of a 100 K gain adjustment potentiometer R12 in the feedback loop. The potentiometer is connected to ground through a 50 K resistor R13.

The offset adjust and clamp circuit 110 is connected to the non-inverting input of adjustable gain amplifier 106. The offset adjust and clamp circuit comprises a 10 K potentiometer R10 connected to +15 v dc supply. The potentiometer wiper is connected to the input of an analog switch 138. The analog switch is enabled and disabled by the output of gating circuit 112 as described hereinafter. When enabled, the switch passes the dc offset voltage at the wiper to the non-inverting input of adjustable gain amplifier 106. The capacitor C2 charges to hold the dc offset voltage. When the analog switch is disabled, the non-inverting input of the amplifier follows the buffer 105 output on the dc offset.

VIS CHANNEL

The VIS channel includes the Si photodiode connected between the inverting input of fixed gain amplifier 114 and ground. The photodiode produces a photovoltaic voltage at the inverting input proportional to the VIS radiation received. The fixed gain amplifier 114 comprises a LM356 operational amplifier whose inverting input is connected to 1 M resistor R28 in the feedback loop. The output of amplifier 114 is connected to adjustable gain filter 116. The adjustable gain filter comprises a LM356 operational amplifier whose inverting input is connected to the amplifier 114 output via a 70 K gain adjustment potentiometer R29 and a 2 K resistor R30. The feedback resistor R31 is 500 K, and the feedback capacitor C3 is 0.001 microfarads. The inverting input of the adjustable gain circuit 116 is connected to the offset adjust circuit 118. The offset adjust circuit includes a 25 K potentiometer R6 connected between +15 v and −15 v dc supplies. The potentiometer wiper is connected by a 300 K resistor R7 to the inverting input of the adjustable gain filter. A diode D1 is connected between resistor R7 and the non-inverting input of the level detector 120. Thus, the offset adjust circuit 118 provides dc offset voltages of proper polarities for the adjustable gain-filter 116 as well as the level detector 120.

The level detector comprises a 3130 operational amplifier whose non-inverting input is connected to 600 K feedback resistor R21 and 10 K input resistor R19. The threshold level is set at the inverting input of the operational amplifier by a divider circuit comprising 49 K resistor R18 and 10 K resistor R20 connected between +5 v dc supply and ground. The threshold is chosen to produce a transition at the level detector output when VIS radiation is blocked from the Si photodiode by wheel 12 or IR filters 46, 50 and an opposite transition when VIS radiation is passed to the Si photodiode by VIS filters 48 and 52. The transitions control the multiplexor 108 via gating circuit 112.

GATING CIRCUIT

Gating circuit 112 includes NAND gates 140, 142, and 144, each of which operate as logic inverters. The level detector output is shifted to a logic compatible level by a divider comprising 100 K resistor R22 and 47 K resistor R23 and fed to NAND gate 140. When VIS radiation is detected in the VIS channel, the level detector 120 produces a logic level "1" at the divider R22-R23, which is inverted by NAND gate 140 so as to enable analog switch 138. The analog switch clamps the non-inverting input of adjustable gain amplifier 106 to the dc offset voltage.

At the same time, the output of NAND gate 140 is re-inverted by NAND gate 142 so as to disable analog switch 146. When disabled, the analog switch disconnects the output of adjustable gain amplifier 106 from the non-inverting input of buffer amplifier 122, thereby cutting off the IR channel.

The output of NAND gate 142 is re-inverted by NAND gate 144. NAND gate 144 controls analog switch 148. The output of NAND gate 144 is the same as the output of NAND gate 140. Accordingly, when analog switch 146 is disabled during VIS radiation detection, NAND gate 144 enables analog switch 148 at the VIS channel input of the analog multiplexer. When enabled, the analog switch transmits the output of adjustable gain filter 116 to the non-inverting input of buffer amplifier 122.

When VIS radiation is transmitted by filter 48 to the densitometer cell, ICG in the blood absorbs radiation at approximately 800 nm, changing the voltage developed by the Si photodiode. The amount of radiation absorbed, hence the change in voltage, depends on the tracer concentration. The change in voltage is reflected at the output of adjustable gain filter 116. The threshold of level detector 120 is chosen so that the greatest expected change in voltage due to presence of the tracer does not trigger the level detector. The connection between the VIS channel and the buffer amplifier 122 therefore remains undisturbed, and the adjustable gain filter output is transmitted to the buffer amplifier through analog switch 148. The buffer amplifier 122 output, which is indicative of the tracer concentration, is then sampled by A/D converter 124 as described more fully hereinafter.

If VIS radiation is not being transmitted to the VIS channel, due to blockage by wheel 12 or filtering by IR filters 46 and 50, the level detector 120 generates a logic level "0" at divider R22-R23 which causes NAND gate 140 to disable analog switch 138. Accordingly, the analog switch releases the input of adjustable gain amplifier 106. The non-inverting input will be at the preset dc offset since capacitor C2 holds the non-inverting input at the dc offset during cut-off of the IR channel. In this manner, the dc offset for the amplifier is prevented from drifting during cut-off of the IR channel. In addition, when VIS radiation is not transmitted to the VIS channel, the level detector causes NAND gate 142 to enable analog switch 146 at the IR channel input of the multiplexer. The analog switch therefore transmits the output of adjustable gain amplifier 106 to buffer amplifier 122. At the same time, NAND gate 144 disables analog switch 148 at the VIS channel input of the multiplexer, disconnecting the output of adjustable gain filter 116 from the buffer amplifier. Thus, the VIS channel is cut-off.

When IR radiation is transmitted by filter 50 to the densitometer cell, DHO in the blood absorbs radiation at approximately 4.0 microns, changing the voltage developed at the PbSe photoresistor. The amount of radiation absorbed, hence the change in voltage, depends on the tracer concentration and is indicated by a change in voltage at the output of adjustable gain amplifier 106. The adjustable gain amplifier output is transmitted to buffer amplifier 122 through analog switch 146. The buffer amplifier 122 output, which is indicative of the tracer concentration, is then sampled by A/D converter 124 as described hereinafter.

SAMPLE DATA ACQUISITION

The sampling rate of A/D converter 124 is determined by the PRF of the one shot circuit 128 output pulses as previously indicated. One shot circuit 128 comprises a 74LS221 monostable multivibrator connected as shown to 1.8 K resistor R32 and 0.001 microfarads capacitor C5. The one shot 128 generates a pulse for each pulse in the CB1 pulse train which is generated continuously by the microprocessor. Each pulse output of the one shot initiates a conversion of the analog output of buffer amplifier 122 to digital. The number of digital samples collected by the microprocessor may be fixed or it may vary with sample level or S/N as determined by the microprocessor software. In performing lung water computations, it is not necessary to vary the number of samples to be collected. However, in detecting the presence of various constituents in gases, it is preferred to vary the number of samples adaptively as described hereinafter.

OPERATION/SOFTWARE

Figure 9A:
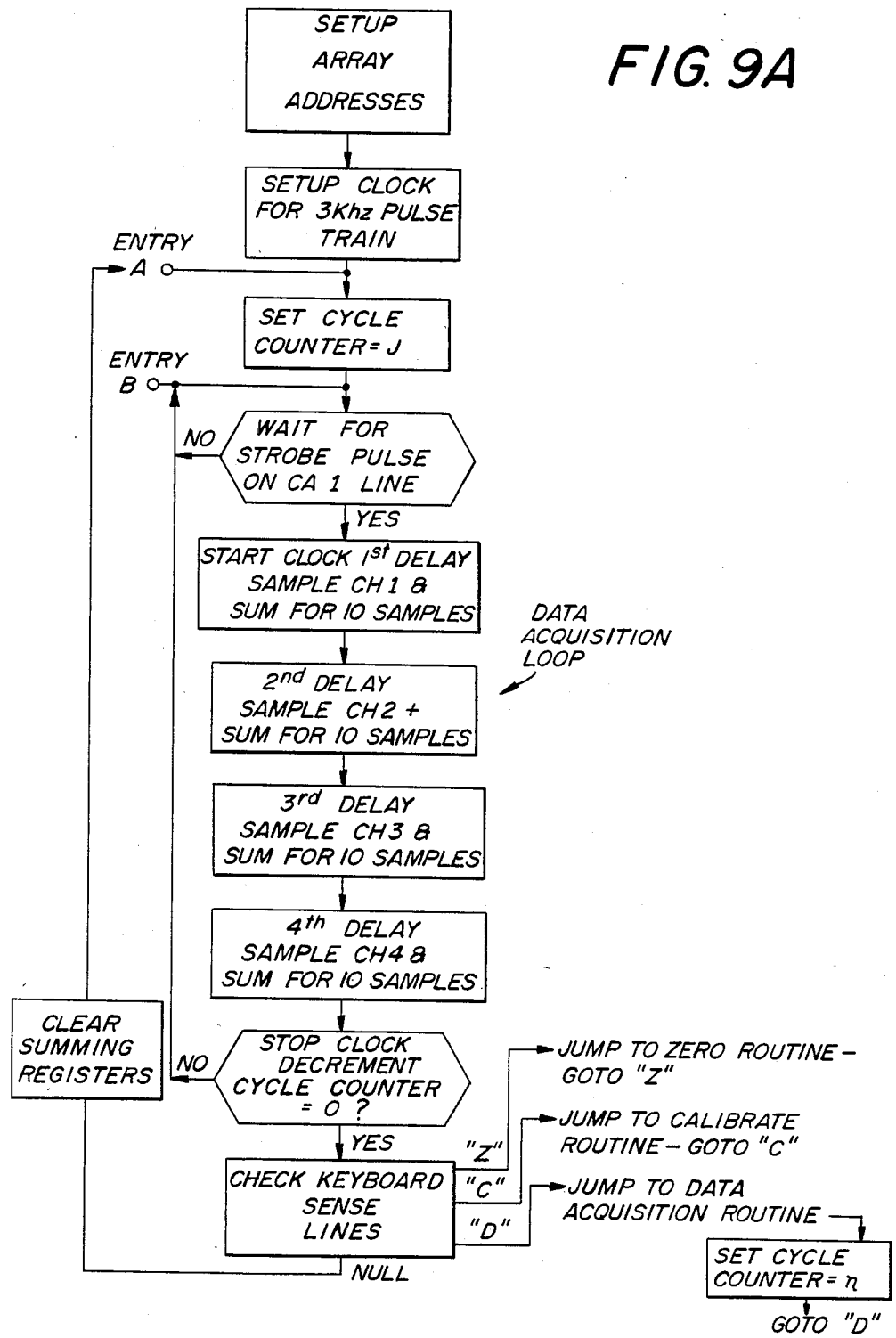
FIGS. 9a and b comprise a flow chart of the software for a data acquisition scheme wherein a fixed number of samples is acquired for each optical filter.
Figure 9B:
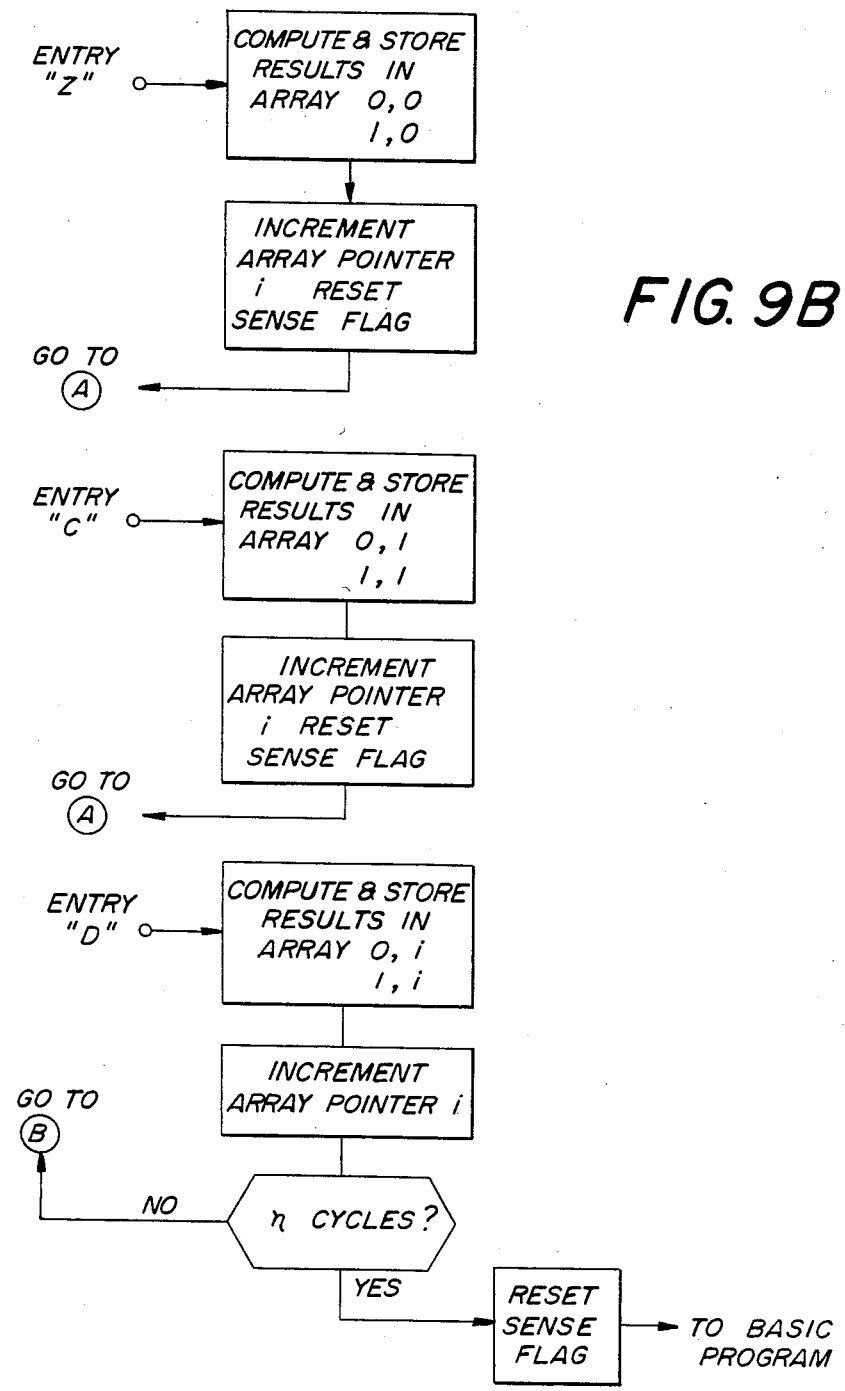
Figure 12:
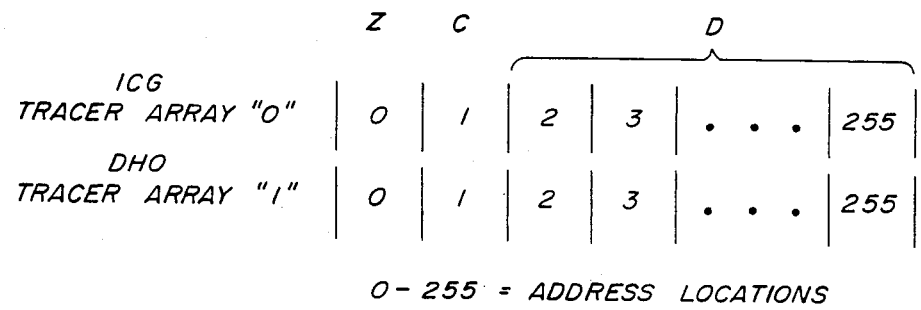
FIG. 12 is a diagram of the memory arrays for the ICG and DHO data.

One embodiment of the software for microprocessor 126 is shown in flow charts in FIGS. 9A and B. The microprocessor first sets up the addresses for a tracer memory array. The array formats are shown in FIG. 12 and described more fully hereinafter. The microprocessor then enters the SET UP CLOCK routine. In this routine, the microprocessor sets up control parameters for a 3 Khz pulse train from a master oscillator or clock. The microprocessor then enters a DATA ACQUISITION LOOP, starting with the SET CYCLE COUNTER=J routine, wherein it sets a cycle counter to a preset number J such as 3. The number indicates the number of revolutions of the chopper/filter wheel 12 for which data samples are to be accumulated. The microprocessor then enters the WAIT FOR STROBE PULSE ON CA1 LINE routine. In this routine, the microprocessor waits for the CA1 trigger pulse from IR sync detector 130.

When the CA1 pulse is received, the microprocessor enters the START CLOCK, FIRST DELAY, SAMPLE CH1 and SUM routine. In this routine, the microprocessor starts the clock pulse train at the CB1 output and begins a continuous count of the CB1 pulses. The microprocessor waits a programmed period of time for overlap of the first filter (46) and lens 26 as indicated by the count of CB1 pulses. The one shot 128 squares up the CB1 pulses and transmits them to the A/D converter. The A/D converter samples the IR channel. After the programmed waiting period, the digitized samples from the A/D convertor are collected by the microprocessor via buffer 130. The microprocessor sums the samples, stores the sum in temporary memory (CH1 summing register). The microprocessor continues to count the CB1 pulses and enters the SECOND DELAY, SAMPLE CH2 AND SUM routine. In this routine, the microprocessor waits a prescribed period of time for overlap between the next filter (52) and lens 26 as indicated by the count of CB1 pulses. After the prescribed period of time, the microprocessor collects the A/D VIS channel samples, sums the samples, and stores the sum in temporary memory (CH2 summing register) and previously indicated. The microprocessor continues to count the CB1 pulses and enters the THIRD DELAY, SAMPLE CH3 AND SUM routine. In this routine, the microprocessor waits a prescribed period of time for the next filter (50) to overlap lens 26 as indicated by the count of CB1 pulses. After the prescribed waiting period, the microprocessor sums the A/D convertor outputs and stores the sum in temporary memory (CH3 summing register). The microprocessor continues to count the CB1 pulses and enters the FOURTH DELAY, SAMPLE CH4 AND SUM routine. After waiting a prescribed period of time for the next filter (48) to overlap lens 26 as indicated by the count of CB1 pulses, the microprocessor sums the A/D converter outputs and stores the sum in temporary memory (CH4 summing register).

It should be noted that the microprocessor continuously counts CB1 pulses as they are generated to determine the waiting periods for each of the DELAY, SAMPLE, CH AND SUM routines. The waiting period for each routine is based on the rotary speed of wheel 12 and the PRF of the CB1 pulses, as well as the spacing between the wheel filters, and corresponds to the time required to bring a wheel filter into the desired overlapping relation with lens 26.

As previously indicated, in the preferred embodiment four optical filters are used in the chopper/filter wheel 12 although only two tracers are being detected. Accordingly, four DELAY, SAMPLE AND SUM routines are required. Two of the routines are used to obtain and sum sample data at the tracer absorption peaks, i.e., at the bandwidths of sample filters 48 and 50 (FIGS. 2 and 6). The other two routines are utilized to obtain and sum sample data to account for drift and changes in the optical density of the blood near the tracer absorption peaks, i.e. at the bandwidths of reference filters 46 and 52 (FIGS. 2 and 6). In general, however, the number of optical filters used in the chopper/filter wheel 12 may be the same as the number of tracers which are to be detected in the fluid sample so that only a like number of DELAY, SAMPLE CH AND SUM routines would be required.

When the microprocessor leaves the last DELAY, SAMPLE AND SUM routine, it enters a STOP CLOCK, DECREMENT CYCLE COUNTER=0? routine. In this routine, the microprocessor stops the CB1 output pulses and the cycle counter is decremented to account for one complete revolution of the chopper/filter wheel. If the cycle counter has not counted down to 0, the microprocessor loops back to the WAIT FOR STROBE PULSE ON CA1 LINE routine and repeats the foregoing operations. When the cycle counter is decremented to 0, corresponding to completion of J revolutions of the wheel 12, the microprocessor enters the CHECK KEYBOARD SENSE LINES routine wherein it sets a sense flag and scans the keyboard output lines "Z", "C", and "D".

ZEROING OPERATION

An active "Z" line indicates that a zeroing operation is required. In the zeroing operation, the densitometer cell is connected to the patient's artery in the manner previously described, but no tracers are injected in the patient's blood. In the zeroing operation, then, data accumulated in the DATA ACQUISITION LOOP corresponds to "blank" blood. If the "Z" line is active, the microprocessor leaves the CHECK KEYBOARD SENSE LINES routine and enters the "Z" routine wherein it computes the average each of the sums computed in the DATA ACQUISITION LOOP i.e. the sum of the samples divided by the number of samples for each of the optical filters, computes the ratio of the averages for the two VIS filters (48, 52) and the ratio of the averages for the two IR filters (46, 50), and stores the ratios in the tracer memory arrays (FIG. 12).

Referring to FIG. 12, the number of memory arrays is equal to the number of tracers to be detected. In the preferred embodiment, two tracers, ICG and DHO, are detected so that there are two memory arrays. Each array comprises 256 address locations, each address location accommodating 2 bytes of data. The ratio computed in the "Z" routine which corresponds to the pair of VIS filters (48, 52) is stored in the first address location of one (ICG) array, and the ratio which corresponds to the pair of IR filters (46, 50) is stored in the first address location of the other (DHO) array. The microprocessor then enters the INCREMENT ARRAY POINTER i AND RESET SENSE FLAG routine. In this routine, the microprocessor increments the array pointers to point to the second address location in each array. In addition, the microprocessor resets the sense flag which had been set upon entering the CHECK KEYBOARD SENSE LINES routine. The microprocessor then re-enters the SET CYCLE COUNTER=J routine and repeats the foregoing operations for a new set of J revolutions of wheel 12. If, after the next set of J revolutions of the chopper/filter wheel, the "Z" line is still active the microprocessor re-enters the "Z" routine. These operations are repeated until the required number of samples has been collected.

CALIBRATE OPERATION

If the "C" output of the keyboard is active when the microprocessor enters the CHECK KEYBOARD SENSE LINES routine, the microprocessor enters the "C" routine. The "C" line is active when it is desired to perform a calibrate operation. In the calibrate operation, the densitometer cell is not connected to the patient. Instead, a sample of the patient's blood containing known quantities of ICG and DHO is recirculated through the densitometer cell, as previously described. Thus, during the calibrate operation, the data acquired and sums computed in the DATA ACQUISITION LOOP correspond to known concentrations of tracers which remain relatively constant.

In the "C" routine, the microprocessor computes the averages corresponding to the sums computed in the DATA ACQUISITION LOOP, computes the ratio of the averages for the VIS filters and the ratio of the averages for the IR filters, and stores the ratios in the second address locations of the tracer memory arrays (FIG. 12). The microprocessor then increments the array pointers i, resets the sense flag, returns to the SET CYCLE COUNTER=J routine, and repeats the operations previously described for a new set of J revolutions of wheel 12. If, after the next set of J revolutions of the wheel, the "C" line is still active, the microprocessor re-enters the "C" routine. These operations are repeated until the required number of samples is collected.

DATA COLLECTION

If the "D" output line of the keyboard is active when the microprocessor enters the CHECK KEYBOARD SENSE LINES routine, the microprocessor enters the "D" routine. The "D" line is active when it is desired to collect data for unknown concentrations of ICG and DHO in the patient's blood so as to enable a computation of lung water. Prior to activating the "D" line, the densitometer cell is connected to the patient's artery and known quantities of ICG and DHO are injected in the patient's blood. Depending on the patient's cardiac output and lung water, varying concentrations of the tracers appear in the blood flowing through the densitometer cell as a function of time. Thus, the data acquired and averages computed in the DATA ACQUISITION LOOP provide an indication of the concentrations of the tracers over time.

In the "D" routine, the microprocessor computes the averages corresponding to the sums calculated in the DATA ACQUISITION LOOP, computes the ratio of the averages for the VIS filters and the ratio of the averages for the IR filters, and stores the ratios in the third locations of the tracer memory arrays. The microprocessor then increments the array pointer i and enters the "n" CYCLES ? routine. In this routine, the microprocessor determines whether a preset number n of ratios has been stored in the memory arrays. As many as 254 ratios may be stored in each memory array since 254 address locations, locations "2" through "255", are available for storage of data in the "D" routine.

If the preset number n of ratios has not been stored in the memory arrays, the microprocessor loops back to the WAIT FOR STROBE PULSE ON CA1 LINE routine in the DATA ACQUISITION LOOP. The microprocessor cycles through the DATA ACQUISITION LOOP J times, corresponding to J revolutions of the chopper/filter wheel, and re-enters the CHECK KEYBOARD SENSE LINES routine. If the "D" sense line is still active, the miroprocessor re-enters the "D" routine and repeats the foregoing operations until the tracer memory arrays have been filled. Thereafter, the microprocessor resets the sense flag and enters the main program wherein the ratios stored in the memory arrays can be retrieved for the purpose of computing tracer concentration and lung water in conventional fashion.

As previously indicated, the chopper/filter wheel 12 need only contain the sample filters, filters 48 (VIS) and 50 (IR), for detecting the ICG and DHO concentrations. The reference filters, filters 52 (VIS) and 46 (IR), can be dispensed with, although they are preferred to enhance S/N. If sample filters only are employed, filters 48, 50, then no ratio is computed in the "Z", "C" and "D" routines. Instead, the average of the sum computed for the VIS filter (48) and the average of the sum computed for the IR filter (50) are computed and directly stored in the tracer memory arrays as already described. The averages are then employed to compute tracer concentration and lung water in the main program in conventional fashion.

In either case, using two or four optical filters, should the microprocessor determine that no keyboard output lines are active, it enters the CLEAR SUMMING REGISTERS ROUTINE wherein the summing registers (temporary memory) which hold the computed sums are cleared. Thereafter, the microprocessor re-enters the SET CYCLE COUNTER=J routine and cycles through the DATA ACQUISITION LOOP as previously described. Accumulated sums are stored in temporary memory (the summing registers), but if none of the keyboard output lines is active the microprocessor clears the sums from memory and re-enters the SET CYCLE COUNTER=J routine, repetitively accumulating and clearing the sums until a zeroing, calibrate or data collection operation is desired as indicated by the "Z", "C" and "D" lines respectively.

SOFTWARE/ADAPTIVE SAMPLING

The foregoing description of software presumes that a fixed number of samples is taken for each of the four optical filters during each revolution of the chopper/filter wheel. If desired, however, the software may be modified so as to automatically vary the number of samples taken for each optical filter during a chopper/filter wheel revolution. This technique is preferred where the absorbance spectrum of one constituent (such as tracer) overlaps the absorbance spectrum of another constituent and the absorbance of one constituent greatly exceeds that of the other constituent. Software for adaptively varying the number of samples is shown in FIGS. 10a-c.

Figure 10A:
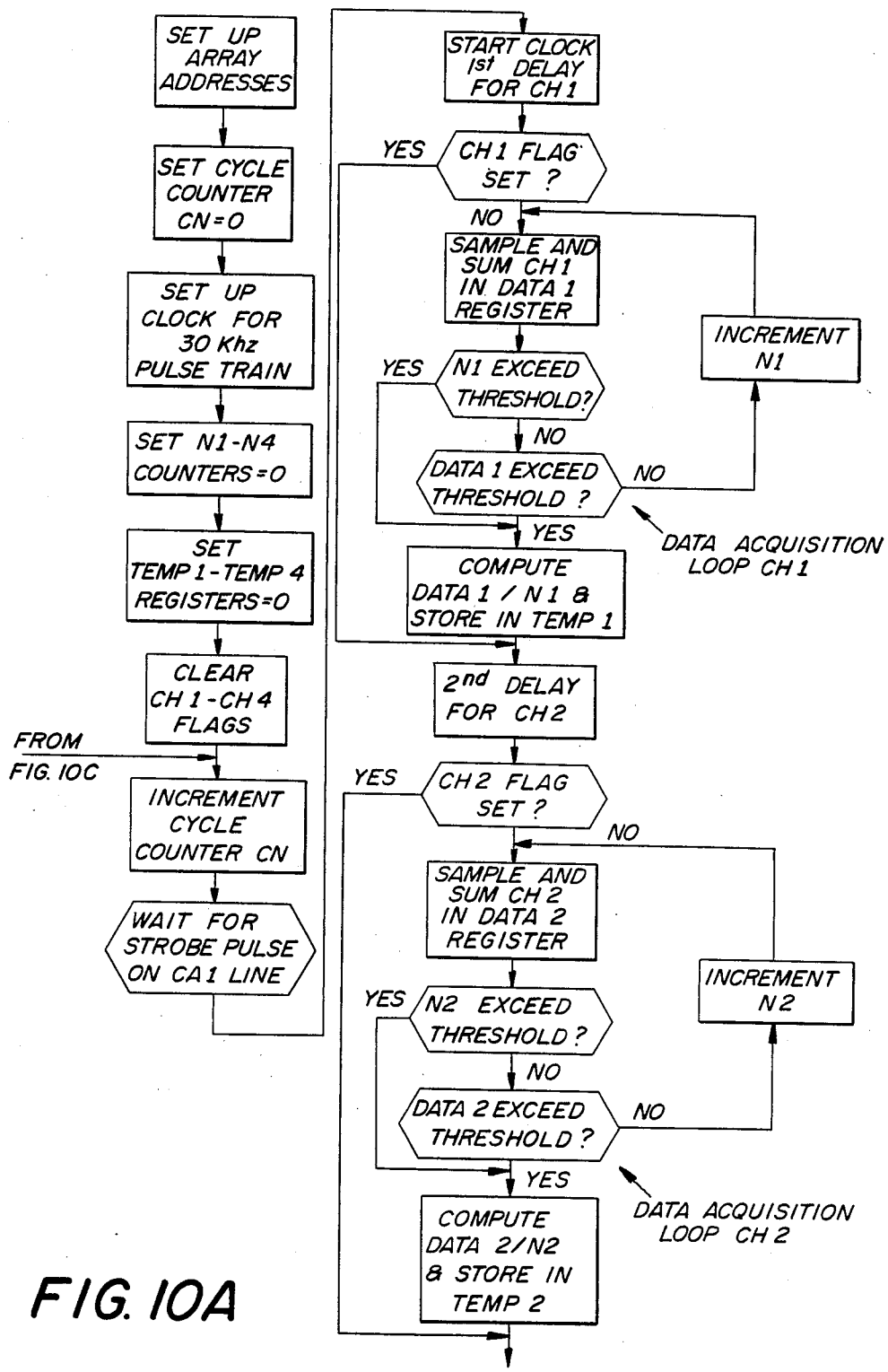
FIGS. 10a–c comprise a flow chart of the software modified to permit adaptive sampling wherein the number of samples acquired for each optical filter is variable.
Figure 10B:
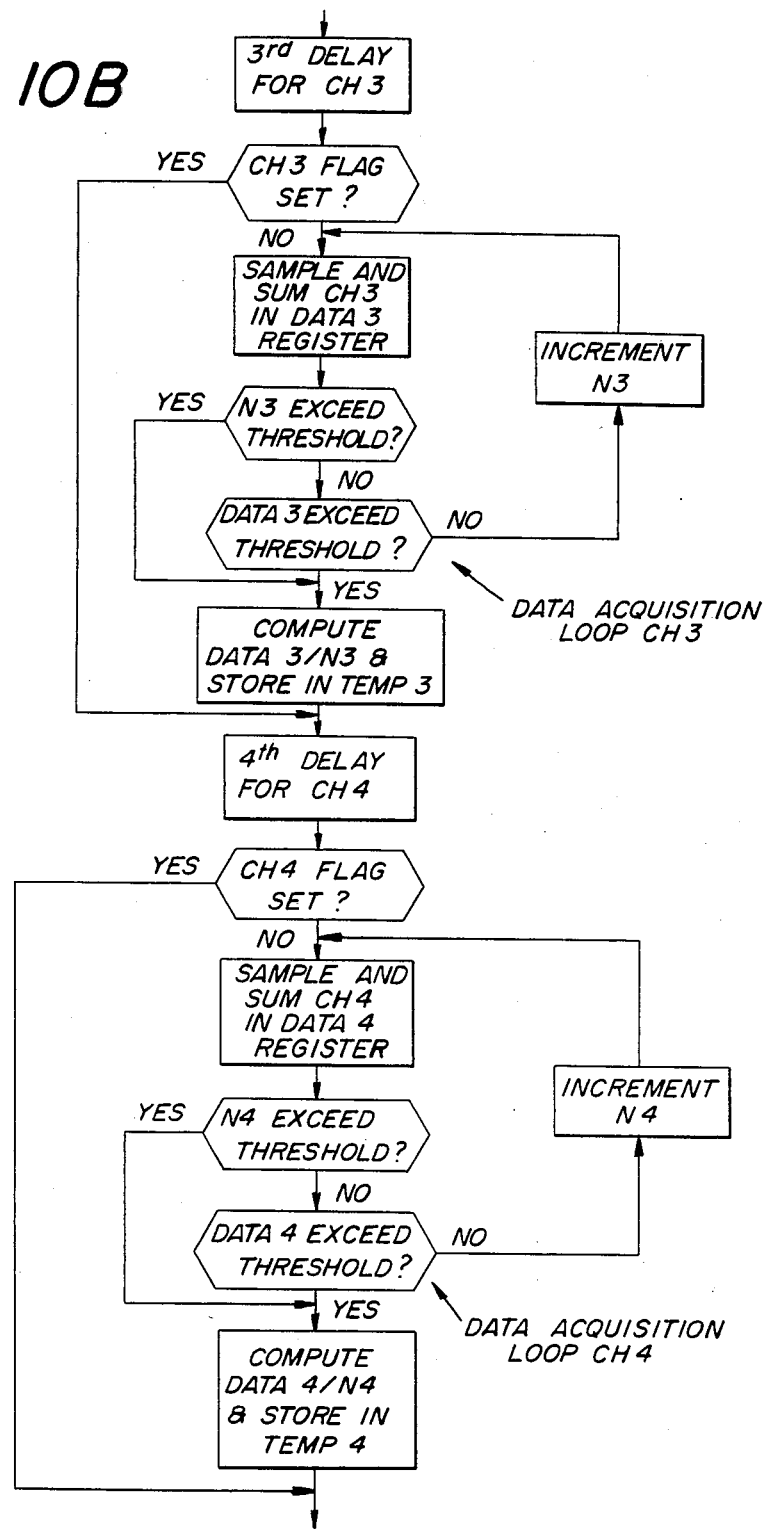
Figure 10C:
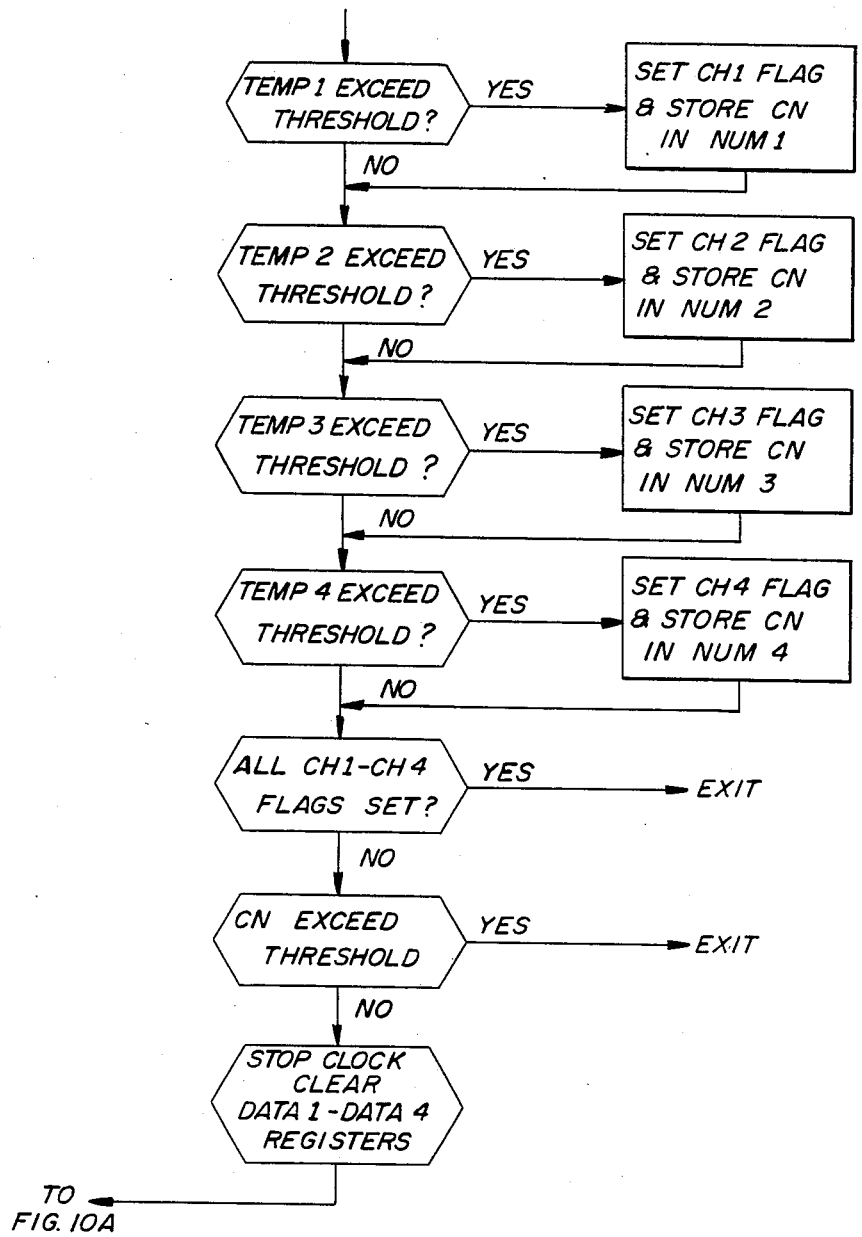

Referring to FIG. 10a, the microprocessor first enters the SET UP ARRAY ADDRESSES routine wherein the tracer array addresses are set up. The microprocessor then sets the cycle counter to zero (SET CYCLE COUNTER CN=0) and sets up control parameters for a clock pulse train, for example 30 Khz, from the master oscillator or clock (SET UP CLOCK 30 Khz PULSE TRAIN). Thereafter, the microprocessor sets counters N1-N4 and registers TEMP1-TEMP4 to zero and clears flags CH1-CH4. The N1-N4 counters count the number of samples accumulated for each optical filter over successive revolutions of the filter wheel. The TEMP1-TEMP4 registers contain the averages of the sums of samples corresponding to each optical filter as described more fully hereinafter. Each of the CH1-CH4 flags is associated with an optical filter. Each flag is set when the average computed for the associated optical filter exceeds a preset threshold, indicating that a sufficient number of samples (not predetermined) has been accumulated for that filter.

The microprocessor then enters the INCREMENT CYCLE COUNTER CN routine (FIG. 10a) wherein the cycle counter is incremented by a count of 1 to indicate the first chopper/filter wheel revolution. The microprocessor then waits for the trigger pulse on the CA1 line. When the trigger pulse is received, the microprocessor enters the data acquisition loop for the first filter (46) (DATA ACQUISITION LOOP CH1), beginning with the START CLOCK, FIRST DELAY FOR CH1 routine. In this routine, the microprocessor counts the CB1 pulses for the predetermined waiting interval, i.e., waits until filter 46 overlaps lens 26. When the filter and lens overlap as indicated by the CB1 pulse count, the microprocessor determines whether the CH1 flag has been set (CH1 FLAG SET?). Since the CH1 flag has not yet been set, the microprocessor enters the SAMPLE AND SUM CH1 IN DATA 1 REGISTER routine. In this routine, the microprocessor takes the first sample during the period of overlap of filter 46 and lens 26 and stores the sample in the DATA 1 register (summing register). The microprocessor then determines whether the N1 counter exceeds a preset threshold representative of the maximum number of samples desired for filter 46. Since the threshold is not yet exceeded, the microprocessor enters the DATA 1 EXCEED THRESHOLD? routine wherein a determination is made as to whether the value stored in the DATA 1 register exceeds a preset threshold corresponding to a maximum value before overflow. The threshold indicates that a sufficient number of samples (not predetermined) has been taken for the filter 46. If the threshold is not exceeded, the microprocessor enters the INCREMENT N1 routine wherein the N1 counter is incremented by one count. This indicates that the first sample has been summed in the DATA 1 register. The microprocessor returns to the SAMPLE and SUM CH1 IN DATA 1 REGISTER routine, adds the next sample value to the DATA 1 register, and cycles through the N1 EXCEED THRESHOLD? and DATA 1 EXCEED THRESHOLD? routines. If the N1 threshold is exceeded, indicating that the desired number of samples has been obtained for filter 46, the microprocessor skips the DATA 1 EXCEED THRESHOLD? routine and proceeds to the COMPUTE DATA 1/N1 AND SUM IN TEMP 1 routine. If the N1 threshold is not exceeded, the microprocessor determines whether the sum of samples in the DATA 1 register exceeds the DATA 1 threshold. If so, the microprocessor enters the COMPUTE DATA 1/N1 AND SUM IN TEMP 1 routine. In this routine, the microprocessor computes the average for the samples acquired for filter 46 by dividing the sum stored in the DATA 1 register by the contents of the N1 counter. The average is stored in the TEMP 1 register.

The microprocessor then enters the data acquisition loop for the second filter (52) (DATA ACQUISITION LOOP CH2), beginning with the SECOND DELAY FOR CH2 routine. In the SECOND DELAY FOR CH2 routine, the microprocessor waits for filter 52 to move into overlapping relation with lens 26 as indicated by the count of CB 1 pulses and repeats the operations previously described in connection with the DATA ACQUISITION LOOP CH1. That is, the microprocessor checks the CH2 flag (CH2 FLAG SET?), sums the samples acquired for filter 52 and holds the sum in the DATA 2 register (SAMPLE AND SUM CH2 IN DATA 2 REGISTER), tests the N2 counter (N2 EXCEED THRESHOLD?) and the DATA 2 register (DATA 2 EXCEED THRESHOLD?) to determine whether a sufficient number of samples has been acquired, increments the N2 counter if a sufficient number of samples has not been acquired, (INCREMENT N2), and computes the average of the samples for filter 52 and stores the same in the TEMP 2 register if a sufficient number of samples has been acquired (COMPUTE DATA 2/N2 AND STORE IN TEMP 2).

The same operations are repeated for filters 50 and 48, in sequence, as indicated in the flow chart in FIG. 10b in connection with the N3, N4, DATA 3, DATA 4, TEMP 3 and TEMP 4 registers. Thus, when the microprocessor exits the COMPUTE DATA 4/N4 AND STORE IN TEMP 4 routine, the microprocessor will have determined that either (1) a preset number of samples has been acquired for each of the optical filters 46, 52, 50 and 48 or (2) a sufficient number of samples (N1, N2, N3, N4-thresholds) has been acquired for each of the filters to enable computation of an average for each sample sum (DATA1, DATA2, DATA3, DATA4 thresholds) corresponding to each filter. Each of the sums will have been stored in the appropriate DATA (summing) register.

The microprocessor then enters the TEMP 1 EXCEED THRESHOLD? routine. See FIG. 10c. In this routine, the microprocessor determines whether the TEMP 1 register has reached a threshold corresponding to a maximum value before overflow. If the threshold has been reached, the microprocessor enters the SET CH1 FLAG AND STORE CN IN NUM 1 routine. In this routine, the microprocessor sets the CH1 flag and stores the contents of the cycle counter CN in a NUM 1 register. The microprocessor then enters the TEMP2 EXCEED THRESHOLD? routine. If the microprocessor determines that the TEMP 1 register has not reached the threshold, it directly enters the TEMP 2 EXCEED THRESHOLD? routine. In each of the TEMP 2 EXCEED THRESHOLD?, TEMP 3 EXCEED THRESHOLD? and TEMP 4 EXCEED THRESHOLD? routines, the microprocessor repeats the foregoing operations, setting the CH2, CH3 and CH4 flags as necessary. In each of these routines, the microprocessor stores the contents of the cycle counter CN in a NUM 2, NUM 3 or NUM 4 register if the threshold of the corresponding TEMP register has been reached. The setting of the CH flag, then, indicates that no further samples should be acquired for the particular optical filter during subsequent revolutions, if any, of the chopper/filter wheel.

If a CH flag has been set, the microprocessor does not sum any of the samples available at the A/D converter outputs during the period of overlap of the particular optical filter and lens 26, i.e., during the corresponding DATA ACQUISITION LOOP. Instead, the microprocessor jumps directly from the CH FLAG SET? routine to the DELAY FOR CH routine for the next optical filter i.e., in the next DATA ACQUISITION LOOP. See FIGS. 10a and 10b. If a CH flag has been set, the contents of the cycle counter have been stored in the appropriate NUM register, providing a record of the number of revolutions of the chopper/filter wheel over which samples have been acquired for the particular optical filter i.e., for the particular DATA ACQUISITION LOOP.

Upon exiting the TEMP 4 EXCEED THRESHOLD? routine, the microprocessor enters the ALL CH1-CH4 FLAGS SET? routine. If all CH flags have been set, this indicates that no further samples should be acquired in any DATA ACQUISITION LOOP. Accordingly, the microprocessor exits the routine and enters the main program wherein the averages for each of the optical filters, as stored in the TEMP registers, are used to compute absorbance of a constituent (such as a tracer) in conventional fashion. If one or more of the CH flags have not been set, the microprocessor enters the CN EXCEED THRESHOLD routine wherein it checks the cycle counter to determine whether the counter has reached a preset threshold representative of the desired number of revolutions of the chopper/filter wheel. If the threshold has been reached, the microprocessor exits the routine and enters the main program wherein absorbance is computed based on the averages stored in the TEMP registers. If the CN threshold has not been reached, the microprocessor clears the DATA 1-DATA 4 registers and loops back to the INCREMENT CYCLE COUNTER CN routine. See FIG. 10a.

The microprocessor thereafter checks each of the CH flags in sequence and acquires samples for each optical filter provided that the corresponding CH flag has not been set. The samples are summed and averaged as previously explained until all of the CH flags have been set or until the cycle counter threshold is reached.

It should be appreciated that the foregoing program enables the number of samples acquired for each optical filter to be varied based on the levels of the samples accumulated, i.e., based on S/N. Thus, for low sample levels in the presence of a high concentration of an interfering substance (low S/N) more samples must be accumulated before the thresholds of the DATA or TEMP registers are reached. Conversely, for high sample levels in the presence of a low concentration of an interfering substance (high S/N) less samples need be accumulated before the DATA or TEMP register thresholds are reached.

OTHER APPLICATIONS

The present invention is useful in a wide variety of applications. For example, the invention may also be applied to determine the color and content of food stuffs, to determine the presence of ground minerals in ground surveys, and to determine the presence of various constituents in gases. Typical arrangements and modifications are shown in FIGS. 13-15.

Figure 13:
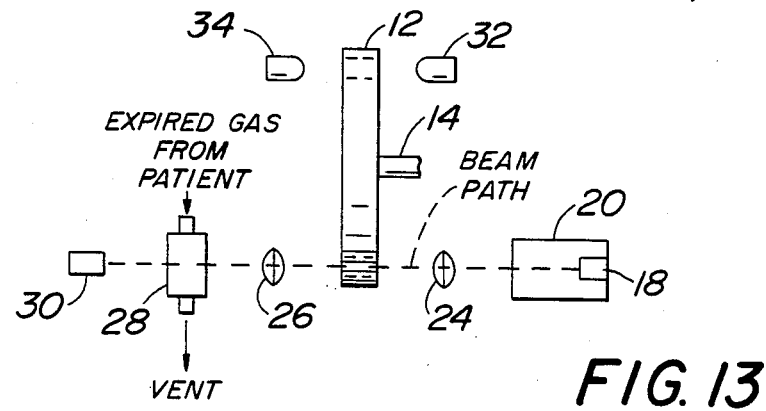
FIG. 13 is a diagrammatic representation of the invention as applied in detecting anesthetic or other gases in the air expired by a patient.

Referring to FIG. 13, the invention is shown as applied to detect the constituents of a gas, such as the presence of anesthetic gases in the air expired from a patient. In this application, anesthetic gases may be monitored quickly and accurately. The air expired by the patient flows by suitable conduits connected to the densitometer cell 28 through the densitometer cell and into a venting chamber (not shown). The OPL of the densitometer cell is preferably 0.5 cm. A mercury cadmium telluride detector 30' is substituted for the two color detector previously described. The optical filters in the chopper/filter wheel are arranged in pairs as previously described. One filter in each pair is an IR filter centered on the absorption peak of the particular anesthetic gas to be detected and the other filter is an IR filter centered on a nearby wavelength. To employ the same electronics (FIG. 7) to acquire the samples for each IR filter, a VIS filter is interposed between consecutive IR filters so as to provide VIS radiation to the VIS channel circuit. The VIS radiation is required to activate the VIS channel and thereby preset the dc offset voltage for the IR channel as previously described. VIS filter data, however, would be ignored by the microprocessor. The software would be as previously described.

Figure 14:
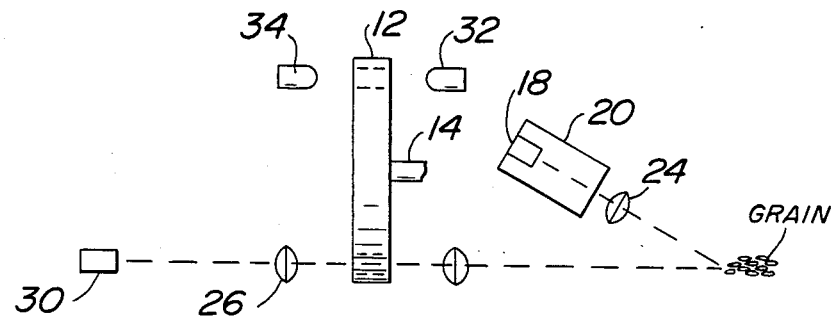
FIG. 14 is a diagrammatic representation of the invention as applied in detecting the color and content of foodstuffs.
Figure 15:
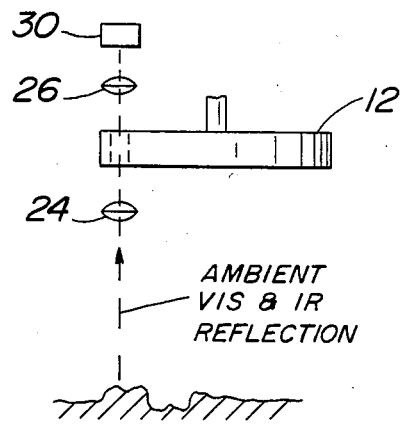
FIG. 15 is a diagrammatic representation of the invention as applied in detecting ground minerals and terrain color in an airborne scanner.

Referring to FIG. 14, there is shown an application of the invention in detecting the color and/or content of foodstuffs such as grain or cereal. In this application, the densitometer cell is dispensed with. Moreover, the radiation incident on the chopper/filter wheel is reflected from the foodstuff rather than being directly transmitted from the VIS and IR source 18. The optical filters on chopper/filter wheel 12 would be arranged in VIS filter pairs and IR filter pairs as previously described. The IR filters are employed to detect content whereas the VIS filters are employed to detect color. One filter in each IR pair is centered on the absorption peak of a particular constituent of interest and the other filter in the IR pair is centered on a different wavelength. The constituents of the foodstuff may be fats, carbohydrates or proteins. A VIS filter is interposed between consecutive IR filters so as to activate the VIS channel as previously described to preset the dc offset voltage of the IR channel.

The VIS filters are arranged in pairs as previously described. One filter in each VIS filter pair is centered on a bandwidth corresponding to a particular color or hue, and the other filter in the pair is centered on a different wavelength. The same electronics (FIG. 7) are employed to acquire the samples for each IR and VIS filter. The software, too, would be the same.

Referring to FIG. 15, there is shown an application of the invention in an airborne scanner for performing ground mineral surveys and detecting terrain color. In this application, the ambient VIS and IR radiation reflected from the ground surface is collimated by lens 24, chopped and filtered by wheel 12, collected by lens 26, and detected by two color detector 30. The optical filters on the wheel 12 are arranged in VIS and IR pairs as previously described. The IR filters are employed to detect mineral content whereas the VIS filters are employed to detect terrain color. One filter in each IR pair is centered on the absorption peak of a mineral of interest. The other IR filter in the pair is centered on a different wavelength. Consecutive IR filters are separated by a VIS filter which serves to pass VIS radiation to the VIS channel so as to preset the dc offset of the IR channel. The VIS filters are arranged in pairs as previously described. One filter in each VIS filter pair is centered on a bandwidth corresponding to a particular color or hue, and the other filter in the pair is centered on a different wavelength. The same electronics (FIG. 7) are employed to acquire the samples for each filter. The software would be the same.

The present invention may be embodied in other specific forms without departing from the spirit or essential attributes thereof and, accordingly, reference should be made to the appended claims, rather than to the foregoing specification, as indicating the scope of the invention.

I claim:

1. Apparatus for detecting concentrations of n tracers in a fluid sample wherein n is an integer greater than or equal to one, comprising:

a single optical channel including a source of a beam of visible (VIS) and infrared (IR) radiation, a densitometer cell having a fluid channel adapted to receive said fluid sample containing said n tracers and an optical channel for transmitting VIS and IR radiation through said fluid sample in said fluid channel, said densitometer cell optical channel forming part of said single optical channel, a motorized rotary chopper/filter wheel containing at least n spaced optical filters, each filter having a bandwidth centered on the wavelength of an absorption peak of at least one of said n tracers, said n filters being arranged so as to intersect said VIS and IR beam in sequence as said wheel is rotated such that said wheel alternately blocks said VIS and IR beam and transmits VIS radiation in a bandwidth of one of said filters or IR radiation in a bandwidth of another of said filters to said densitometer cell optical channel, the level of VIS or IR radiation transmitted through said sample being proportional to the concentration of a tracer in said sample, VIS and IR sensors in-line with said densitometer cell optical channel for separately sensing filtered VIS radiation and filtered IR radiation transmitted through said fluid sample in said densitometer cell and for producing a VIS output signal proportional to the sensed VIS radiation and a separate IR output signal proportional to the sensed IR radiation, and means for electronically sampling said VIS sensor output signal and said IR sensor output signal as said filters intersect said VIS and IR beam in synchronism with the rotation of said wheel including separate VIS and IR electronic channels, said VIS electronic channel being coupled to said VIS sensor and said IR electronic channel being coupled to said IR sensor, means for enabling one of said electronic channels while disabling the other based on the level of the sensor output signal in the enabled channel including means for clamping the dc level of the disabled channel, wherein each sample of said VIS sensor output signal is proportional to the concentration of a tracer and each sample of said IR sensor output signal is proportional to the concentration of another tracer.

2. Apparatus according to claim 1 including means for separately accumulating plural samples of said VIS sensor output signal and plural samples of said IR sensor output signal for each revolution of said wheel, and means for computing the average of said accumulated samples of said VIS sensor output signal and the average of said accumulated samples of said IR sensor output signal for each revolution of said wheel.

3. Apparatus according to claim 1 wherein said n tracers are DHO and ICG.

4. Apparatus according to claim 3 wherein one of said n filters has a bandwidth centered on the wave length of the absorption peak of DHO and another of said n filters has a bandwidth centered on the wave length of the absorption peak of ICG.

5. Apparatus according to claim 4 wherein said chopper/filter wheel further includes a reference filter having a bandwidth centered near the wavelength of the absorption peak of DHO and another reference filter having a bandwidth centered near the wavelength of the absorption peak of ICG.

6. Apparatus according to claim 5 wherein the bandwidth of said reference filter centered near the wavelength of the absorption peak of DHO is centered on approximately 3.6 microns and wherein the bandwith of said reference filter centered near the wavelength of the absorption peak of ICG is centered on approximately 700 nanometers.

7. Apparatus in accordance with claim 1 wherein said optical channel of said densitometer cell is provided with optical filter means for filtering VIS and IR radiation between approximately 350 nanometers and 4.6 microns.

8. Apparatus according to claim 1 wherein said means for electronically sampling further includes an A/D converter, an analog multiplexer for alternately transmitting the outputs of said VIS and IR electronic channels to said A/D converter, and means for causing said A/D converter to repetitively sample the output of said analog multiplexer and to convert each sample to a digital signal.

9. Apparatus according to claim 1 wherein said means for electronically sampling includes means for sampling said VIS and IR sensor output signals a preset number of times as each of said filters intersects said VIS and IR beam.

10. Apparatus according to claim 1 wherein said means for electronically sampling includes means for adaptively sampling said VIS and IR sensor output signals a variable number of times depending on the levels of said sensor output signals as each of said filters intersect said VIS and IR beam.

11. Lung water computer system for detecting concentrations of DHO and ICG tracers in a blood sample, comprising:

a single optical channel including a source of a beam of visible (VIS) and infrared (IR) radiation, a densitometer cell having a fluid channel adapted to receive a blood sample containing said ICG and DHO tracers and an optical channel intersecting said fluid channel for transmitting VIS and IR radiation through said blood sample in said fluid channel, said densitometer cell optical channel forming part of said single optical channel, a motorized rotary chopper/filter wheel containing at least two spaced optical filters, each filter having a bandwidth centered on the wavelength of an absorption peak of one of said ICG and DHO tracers, said filters being arranged so as to intersect said VIS and IR beam in sequence as said wheel is rotated such that said wheel alternately blocks said VIS and IR beam and transmits VIS radiation in a bandwidth of one of said filters or IR radiation in a bandwidth of another of said filters to said densitometer cell optical channel, the level of VIS or IR radiation transmitted through said sample being proportional to the concentration of a tracer in said sample, VIS and IR sensors in-line with said densitometer cell output channel for separately sensing filtered VIS radiation and filtered IR radiation transmitted through said blood sample in said densitometer cell and for producing a VIS output signal proportional to the sensed VIS radiation and a separate IR output signal proportional to the sensed IR radiation, and means for electronically sampling said VIS sensor output signal and said IR sensor output signal as said filters intersect said VIS and IR beam in synchronism with the rotation of said wheel including separate VIS and IR electronic channels, said VIS electronic channel being coupled to said VIS sensor and said IR electronic channel being coupled to said IR sensor, means for enabling one of said electronic channels while disabling the other based on the level of said VIS sensor output signal including means for clamping the dc level of said IR channel when said IR channel is disabled, wherein each sample of said VIS sensor output signal is proportional to the concentration of said ICG tracer and each sample of said IR sensor output signal is proportional to the concentration of said DHO tracer.

12. The lung water computer system according to claim 11 including means for separately accumulating plural samples of said VIS sensor output signal and plural samples of said IR sensor output signal for each revolution of said wheel, and means for computing the average of said accumulated samples of said VIS sensor output signal and the average of said accumulated samples of said IR sensor output signals for each revolution of said wheel.

13. The lung water computer system according to claim 11 wherein said chopper/filter wheel is provided with an optical reference filter having a bandwidth centered near the wavelength of the absorption peak of DHO and another optical reference filter having a bandwidth centered near the wavelength of the absorption peak of ICG.

14. The lung water computer system according to claim 11 wherein the bandwidth of the reference filter centered near the wavelength of the absorption peak of DHO is centered on approximately 3.6 microns and wherein the bandwidth of the reference filter centered near the wavelength of the absorption peak of ICG is centered on approximately 700 nanometers.

15. The lung water computer system according to claim 11 wherein said optical channel of said densitometer cell is provided with optical filter means for filtering VIS and IR radiation between approximately 350 nanometers and 4.6 microns.

16. The lung water computer system according to claim 15 wherein said means for electronically sampling further includes an A/D converter, an analog multiplexer for alternately transmitting the outputs of said VIS and IR electronic channels to said A/D converter, and means for causing said A/D converter to repetitively sample the output of said analog multiplexer and to convert each sample to a digital signal.

* * * * *